US006844213B2

(12) United States Patent
Sparks

(10) Patent No.: US 6,844,213 B2
(45) Date of Patent: Jan. 18, 2005

(54) PROCESS OF FORMING A MICRONEEDLE AND MICRONEEDLE FORMED THEREBY

(75) Inventor: Douglas Ray Sparks, Whitmore Lake, MI (US)

(73) Assignee: Integrated Sensing Systems, Ypsilanti, MI (US)

( * ) Notice: Subject to any disclaimer, the term of this patent is extended or adjusted under 35 U.S.C. 154(b) by 345 days.

(21) Appl. No.: 10/063,117

(22) Filed: Mar. 22, 2002

(65) Prior Publication Data

US 2002/0193818 A1 Dec. 19, 2002

Related U.S. Application Data

(60) Provisional application No. 60/297,775, filed on Jun. 14, 2001.

(51) Int. Cl.[7] .............................................. H01L 21/00
(52) U.S. Cl. ............................. 438/41; 438/42; 438/44; 438/53
(58) Field of Search ......................... 438/40–45, 49–53

(56) References Cited

U.S. PATENT DOCUMENTS

2002/0138049 A1 * 9/2002 Allen et al. ................. 604/272

* cited by examiner

Primary Examiner—H. Jey Tsai
(74) Attorney, Agent, or Firm—Gary M. Hartman; Domenica N. S. Hartman; Hartman & Hartman, P.C.

(57) ABSTRACT

A microneedle and a process of forming the microneedle of single-crystal silicon-based material without the need for deposited films. The microneedle comprises a piercing end, an oppositely-disposed second end, and an internal passage having an opening adjacent the piercing end. The cross-section of the microneedle, and therefore the passage within the microneedle, is defined by first and second walls formed of doped single-crystal silicon-based material and separated by the passage, and first and second sidewalls separated by the passage, sandwiched between the first and second walls, and formed of single-crystal silicon-based material that is more lightly doped than the first and second walls.

20 Claims, 3 Drawing Sheets

PROCESS OF FORMING A MICRONEEDLE AND MICRONEEDLE FORMED THEREBY

CROSS REFERENCE TO RELATED APPLICATIONS

This application claims the benefit of U.S. Provisional Application No. 60/297,775, filed Jun. 14, 2001.

BACKGROUND OF INVENTION

1. Field of the Invention

The present invention generally relates to cannula and similar hollow needle-like devices. More particularly, this invention relates to a method of forming miniature needle-like devices from single-crystal silicon-based material using micromachining and wafer bonding techniques.

2. Description of the Related Art

Medical delivery of drugs has been accomplished for many years using cannula and hollow needles. Metal needles have been miniaturized to very small sizes and integrated with attachments to increase functionality. However, the extent to which metal needles can be miniaturized is limited by processing limitations and the ductility of metals, the latter of which renders metal needles with small diameters prone to bending. In contrast, cannula and needles formed of silicon and silicon-based alloys such as SiGe and SiGeB are not ductile at room temperature and can be micromachined to a much smaller size, typically less than 100 micrometers in diameter, resulting in what is termed herein a microneedle. Because of this capability for greater miniaturization, there is considerable interest in fabricating cannula and other needle-like devices from silicon-based materials.

Silicon microneedles have typically been formed by a combination of micromachining and deposited layers. For example, U.S. Pat. No. 5,855,801 to Lin et al. discloses a process of forming microneedle a by wet anisotropic etching single-crystal silicon and depositing silicon nitride to define a microchannel within the microneedle. U.S. Pat. No. 5,928,207 to Pisano et al. discloses a process by which a silicon microneedle is fabricated by wet isotropic etching single-crystal silicon and depositing polysilicon. Another process described in K. Papageorgiou et al., "A Shuttered Probe with In-Line Flowmeters for Chronic In-Vivo Drug Delivery" combines reactive ion etching (RIE) a pattern of diagonal openings in the surface of a silicon substrate to define a grating, undercutting the grating by anisotropic etching to define a microchannel beneath the grating, and then sealing the openings of the grating with deposited films of silicon oxide, silicon nitride or polysilicon."

A drawback to the use of deposited films of silicon oxide, silicon nitride, polysilicon, etc., on a single-crystal silicon micromachined features is the stress that results from grain size variation within deposited films and differences in coefficients of thermal expansion between the deposited films an single-crystal silicon. Such stresses increase the risk of bowing, warping and cracking of the micromachined features, which can lead to mechanical problems and high scrappage rates in the case of cannula and other types of microneedles. Deposited films also limit the wall thickness and internal cross-sectional area of microneedles, thereby limiting the degree to which a microneedle can be miniaturized.

SUMMARY OF INVENTION

The present invention provides a microneedle and a process of forming the microneedle of single-crystal silicon-based material without the need for deposited films. As a result, the present invention avoids the processing and mechanical problems associated with microneedles formed of deposited films on single-crystal silicon.

According to a first aspect of the invention, the device of this invention includes a needle member comprising a piercing end and an oppositely-disposed second end, and an internal passage having an opening adjacent the piercing end. The cross-section of the needle member, and therefore the passage within the needle member, is defined by first and second walls formed of doped single-crystal silicon-based material and separated by the passage, and first and second sidewalls separated by the passage, sandwiched between the first and second walls, and formed of a single-crystal silicon-based material that is more lightly doped than the first and second walls. Accordingly, the structural components that define the passage within the needle member are not required to be formed of a deposited film.

The process of this invention generally entails providing a first wafer having a first layer of doped single-crystal silicon-based material and a top layer of doped single-crystal silicon-based material on the first layer, with the top layer being more lightly doped than the first layer. A cavity is etched in the top layer so that the top layer defines the first and second sidewalls, which this time are separated by the cavity. The first wafer is then bonded to a second wafer having a second layer of doped single-crystal silicon-based material, so that the top layer is sandwiched between the first and second layers of the first and second wafers, respectively. Similar to the first layer of the first wafer, the second layer of the second wafer is more heavily doped than the top layer of the first wafer. As a result of the bonding step, the cavity etched in the top layer of the first wafer is delimited by first and second walls defined by the first and second layers, respectively, as well as the first and second sidewalls, yielding the internal passage of the needle member. The first and second wafers are then etched to define the needle member by removing portions of the first, second and top layers to define the piercing and second ends of the needle member, and the opening to the passage adjacent the piercing end.

In view of the above, the present invention can be seen as forming a hollow tube using slices (wafers) of single-crystal silicon-based material and wafer bonding techniques, thereby eliminating the requirement for deposited layers and the potential for processing and mechanical problems associated with deposited films on single-crystal silicon. Plasma etching techniques are preferably used to remove portions of the first, second and top layers of the wafers to produce the desired outer perimeter shape of the needle member, including a sharp, tapered point at the piercing end of the needle member. Differences in the doping levels within the layers of the wafers enable etching techniques to be used to minimize the thicknesses of the first and second sidewalls and the first and second walls of the needle member, such that the outer and inner dimensions of the needle member can be minimized.

Other objects and advantages of this invention will be better appreciated from the following detailed description.

DETAILED DESCRIPTION

Figure 9:
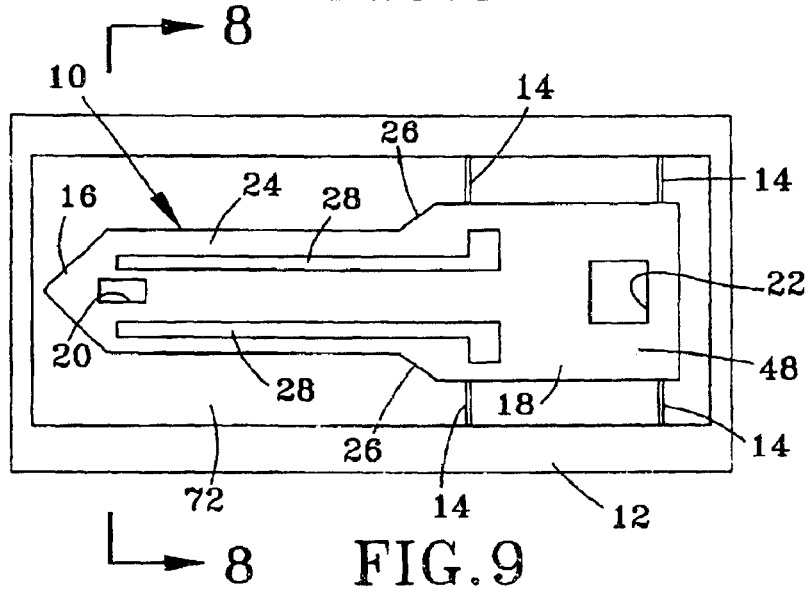
FIG. 9 is a plan view of a microneedle produced by the method of FIGS. 1 through 8.

FIG. 9 represents a microneedle, more particularly a cannula 10, suspended within a frame 12 as a result of preferred processing steps of the present invention. While the invention will be discussed in reference to the cannula 10, essentially any type of microneedle can be fabricated in accordance with the invention, and such microneedles can differ significantly in appearance from the cannula 10 of FIG. 9.

The cannula 10 is shown as being suspended within the interior of the frame 12 by a number of tabs 14, but otherwise separated from the frame 12 by a trench 72 that delineates the outer perimeter of the cannula 10. In this configuration, the cannula 10 can be singulated from the frame 12 by breaking the tabs 14. The cannula 10 can be one of any number of a cannula fabricated in a wafer, in which case the frame 12 would be one of any number of interconnected frames. The cannula 10 is depicted as having a sharp piercing end 16 and a wider second end 18 suitable for attachment to a tube or other conduit (not shown) for delivering fluid to the cannula 10. A pair of fluid ports 20 and 22 are shown as having been formed in a wall 48 of the cannula 10. When using the cannula 10 to deliver a fluid, the port 20 located adjacent the piercing end 16 serves as the fluid outlet, while the port 22 located adjacent the second end 18 of the cannula 10 is the fluid inlet. The cannula 10 has a shaft portion 24 between its piercing and second ends 16 and 18, with the shaft portion 24 being narrower than the second end 18 as a result of a tapered shoulder 26 therebetween.

A pair of electrodes 28 are shown as having been formed on the same wall 48 as the inlet and outlet ports 20 and 22. The electrodes 28 are optional features of the invention, and allow for biochemical monitoring, stimulation functions, etc., as the cannula 10 is used to deliver or extract a fluid. Suitable materials for the electrodes 28 include such biocompatible metals as titanium, platinum and iridium. Electrical devices (not shown) can be fabricated in and on the surface of the wall 48 of the cannula 10 to assist in the monitoring and stimulation functions.

Figure 1:
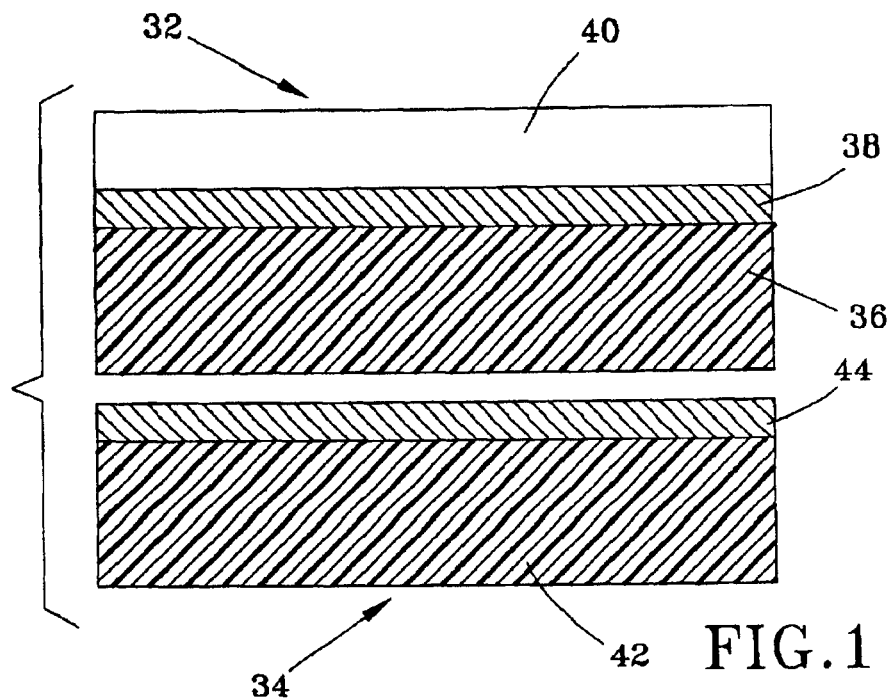
FIGS. 1 through 8 represent processing steps in the fabrication of a microneedle in accordance with a preferred embodiment of this invention.
Figure 3:
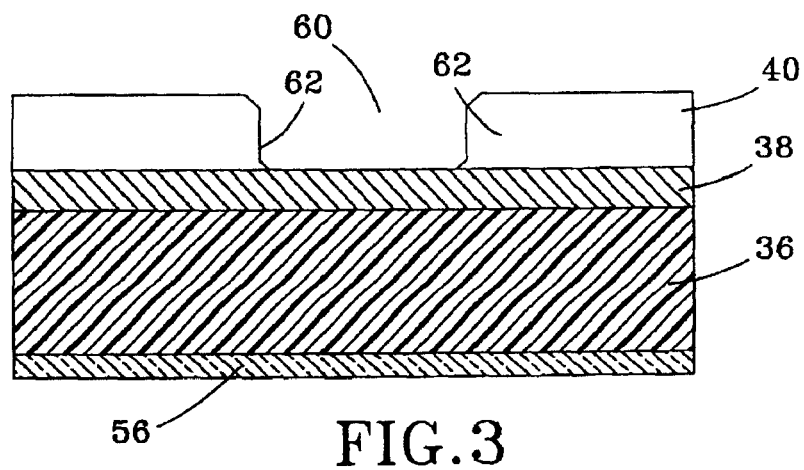

A preferred process for fabricating the cannula 10 of FIG. 9 begins with a pair of wafers 32 and 34, shown in FIG. 1. The wafers 32 and 34 are represented as having lightly-doped p-type single-crystal silicon substrates 36 and 42, respectively. Alternatively, n-type silicon substrates, silicon-on-insulator (SOI) substrates as well as other types of wafers could be used in the process of this invention. A first of the wafers 32 is represented as having two epitaxial layers 38 and 40 grown on its substrate 36. The epitaxial layers 38 and 40 are represented as being formed of a silicon-germanium-boron (SiGeB) alloy (e.g., containing less than 30 weight percent germanium) and silicon, respectively, such that the SiGeB epitaxial layer 38 is hetero-epitaxially aligned with the single-crystal silicon substrate 36, and the Si epitaxial layer 40 is hetero-epitaxially aligned with the SiGeB epitaxial layer 38. Both epitaxial layers 38 and 40 and the substrate 36 are indicated as being doped p-type, i.e., with boron or another trivalent element (an "acceptor-type" impurity). According to one aspect of the invention, the epitaxial layer 38 serves as an etchstop during etching of the epitaxial layer 40, by which sidewalls (50 and 52 in FIG. 8) of the cannula 10 are defined as discussed below (FIG. 3). For this purpose, the epitaxial layer 38 is preferably heavily p-type, e.g., a boron dopant concentration of greater than $1\times10^{19}$ atoms/cc. In comparison, the substrate 36 and epitaxial layer 40 may have dopant concentrations of about $1\times10^{15}$ atoms/cc, such that the epitaxial layer 38 is more heavily doped than the substrate 36 and epitaxial layer 40. Alternatively, the substrate 36 and epitaxial layer 40 could be doped n-type.

With further reference to FIG. 1, the second wafer 32 is represented as having an epitaxial layer 44 grown on its p-type single-crystal silicon substrate 42. As with the wafer 32, the epitaxial layer 44 is represented as being a SiGeB alloy, such that the epitaxial layer 44 is hetero-epitaxially aligned with the single-crystal silicon substrate 42. Also similar to the first wafer 32, the substrate 42 and its epitaxial layer 44 are indicated as being doped p-type, with the epitaxial layer 44 again being doped more heavily than the substrate 42, e.g., a dopant concentration of about $1\times10^{19}$ atoms/cc for the epitaxial layer 44 and a dopant concentration of about $1\times10^{15}$ to about $1\times10^{17}$ atoms/cc for the substrate 42.

The epitaxial layers 38 and 44 of the wafers 32 and 34 will define upper and lower walls (46 and 48 in FIGS. 5 through 8) of the cannula 10, while sidewalls (50 and 52 in FIG. 8) of the cannula 10 will be defined by the epitaxial layer 40 of the wafer 32. According to a preferred aspect of the invention, the thicknesses of the epitaxial layers 38 and 44 ultimately determine the thicknesses of their respective walls 46 and 48, and the thickness of the epitaxial layer 40 ultimately determines the width of the sidewalls 50 and 52. As a result, the outer dimensions of the cannula 10 can be controlled and minimized by selecting appropriate thicknesses for the epitaxial layers 38, 40 and 44. As an example, suitable thicknesses for the epitaxial layers 38, 40 and 44 are in a range of about five to about twenty micrometers, such as about ten micrometers.

Figure 2:
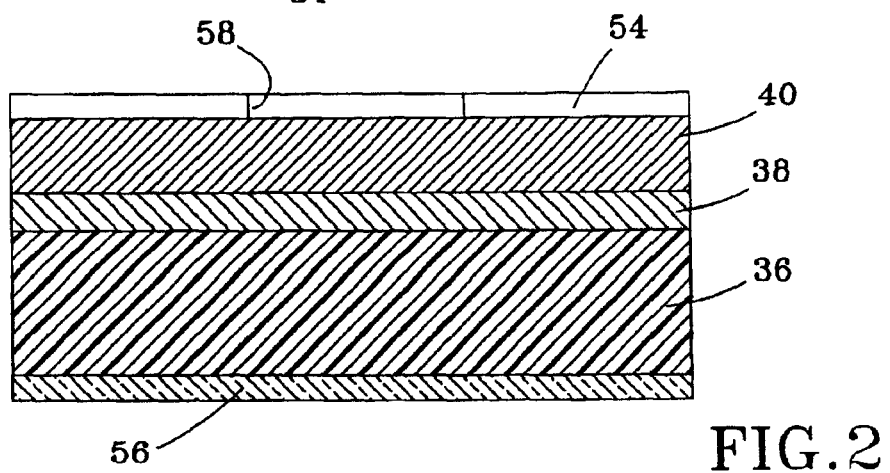

FIG. 2 represents the result of growing or depositing a pair of masking layers 54 and 56 on the epitaxial layer 40 and the backside of the substrate 36, respectively. A suitable material for the masking layers 54 and 56 is silicon dioxide, though other materials could be used, such as silicon nitride or a photoresist material. The masking layers 54 and 56 serve to protect the wafer 32 during silicon etching, and for this purpose are grown or deposited to thicknesses of at least 0.5 micrometers. The masking layer 54 is shown in FIG. 2 as having an opening 58 as a result of the layer 54 having been patterned and etched in any suitable manner, such as chemical etching with hydrofluoric acid (HF) if the masking layer 54 is formed of silicon dioxide. In FIG. 3, a cavity 60 has been formed by etching the epitaxial layer 40 through the opening 58 in the masking layer 54 (which has been stripped). The cavity 60 can be performed by plasma or wet chemical etching, or a combination of both. According to a preferred aspect of the invention, the cavity 60 is formed by a two-step etch process, a first step of which is preferably a timed plasma (anisotropic) etch, followed by a wet chemical etch that uses the heavily-doped epitaxial layer 38 as an etchstop. The plasma etch is timed to remove most but not all of the epitaxial silicon beneath the opening 58 in the masking layer 54. The remaining epitaxial silicon is then removed by wet etching, preferably anisotropically such as with ethylenediamine pyrocatechol (EDP) or potassium hydroxide (KOH). The opposing walls 62 of the cavity 60 will subsequently define the sidewalls 50 and 52 of the cannula 10. Using a plasma etch for the bulk of the etching process enables the sidewalls 50 and 52 of the cannula 10 to be formed substantially perpendicular to the surface of the epitaxial layer 40. Completing the etch process with a wet chemical etching using the heavily-doped epitaxial layer 38 as an etchstop enables the thickness of the epitaxial layer 40 to determine the height of the sidewalls 50 and 52 of the cannula 10. In combination, these etching techniques yield a two-step etching process capable of minimizing the cross-sectional dimensions of the cannula 10.

Figure 4:
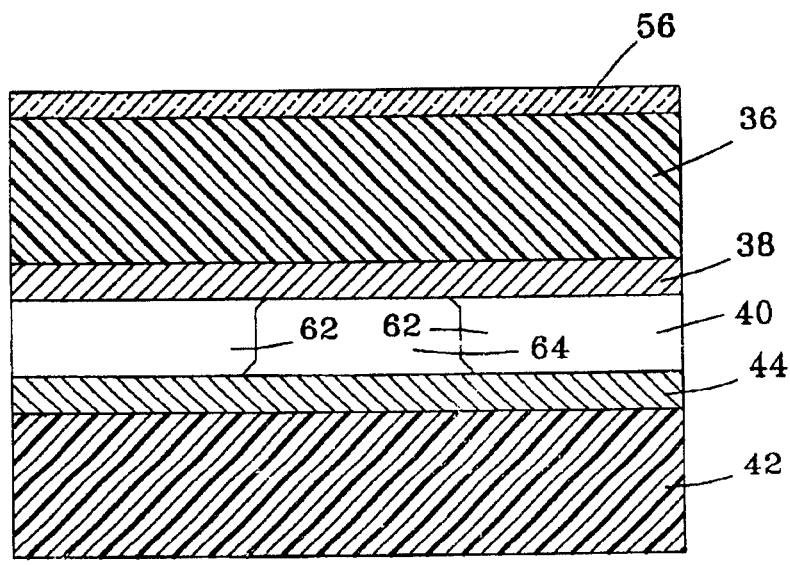

In FIG. 4, the wafers 32 and 34 have been bonded together, with the epitaxial layer 44 of the wafer 34 being bonded to the epitaxial layer 40 of the wafer 32, with the result that the cavity 60 in the epitaxial layer 40 is closed by the epitaxial layer 44 of the second wafer 34, yielding a closed cavity 64 within the wafer stack. A preferred bonding technique is silicon direct bonding (SDB), such as silicon fusion bonding (SFB) to produce a hermetic, covalent bond. For this purpose, the mating surfaces of the layers epitaxial layers 40 and 44 are cleaned and then activated, such as by an HF dip. The wafers 32 and 34 are then aligned, pressed together and annealed at about 900° C. to about 1200° C. for a duration of about one to about twelve hours to permanently bond the epitaxial layers 40 and 44 together.

Figure 5:
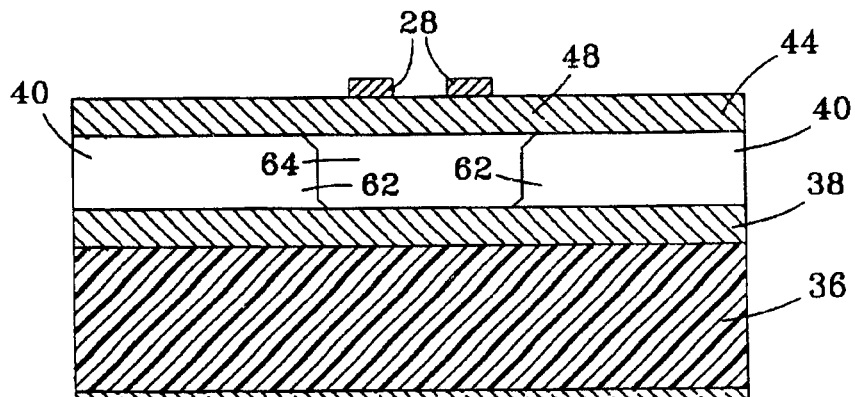
Figure 6:
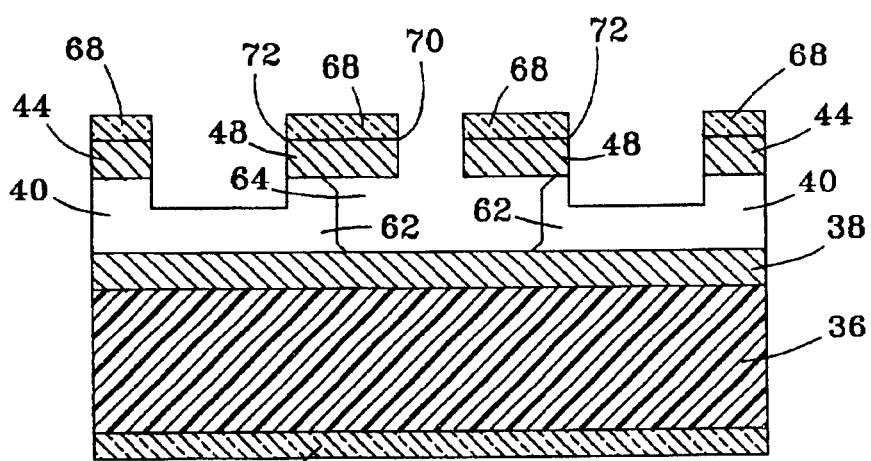

After wafer bonding, the lightly-doped substrate 42 of the second wafer 34 is removed by etching (e.g., EDP) or wafer grinding, thereby the exposing epitaxial layer 44 of the second wafer 34. The portion of the epitaxial layer 44 over the cavity 64 defines one wall 48 of the cannula 10, shown in plan view in FIG. 9. FIG. 5 represents a cross-section through a portion of the wafer stack on which the metal electrodes 28 shown in FIG. 9 have been formed. FIG. 6 represents a cross-section through a different portion of the wafer stack than that shown in FIG. 5, and shows the result of depositing and patterning an oxide mask 68 on the epitaxial layer 44, followed by anisotropically etching the epitaxial layer 44 to form an opening 70 through the wall 48 and a trench 72 with portions to either side of the wall 48. The opening 70 shown in FIG. 6 is the fluid port 20 of FIG. 9, while the trench 72 separates the cannula 10 and the frame 12 in FIG. 9 and therefore defines the outer perimeter of the cannula 10. As seen in FIG. 6, the opening 70 is completely through the epitaxial layer 44 (wall 48), thereby breaching the cavity 64 as required for the port 20. The trench 72 also extends completely through the epitaxial layer 44, but terminates within the epitaxial layer 40. The opening 70 and trench 72 are preferably formed by a timed plasma etch that is stopped soon after the opening 70 breaches the cavity 64.

Figure 7:
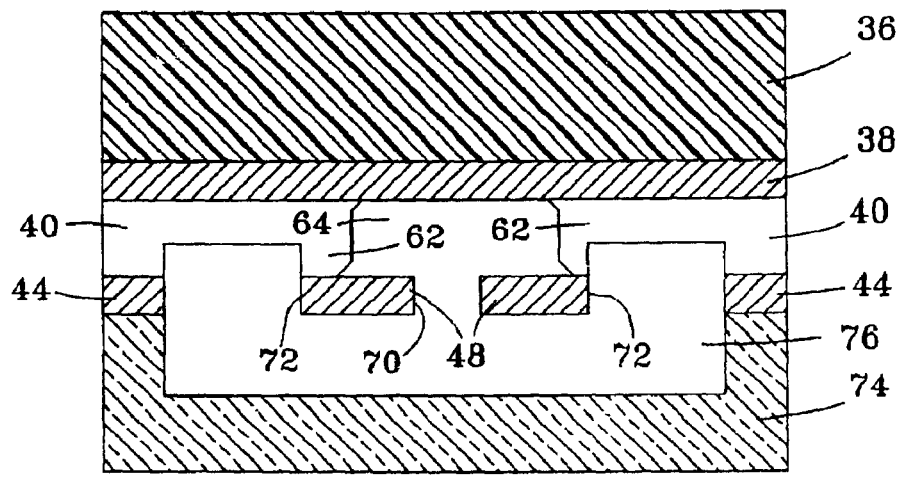
Figure 8:
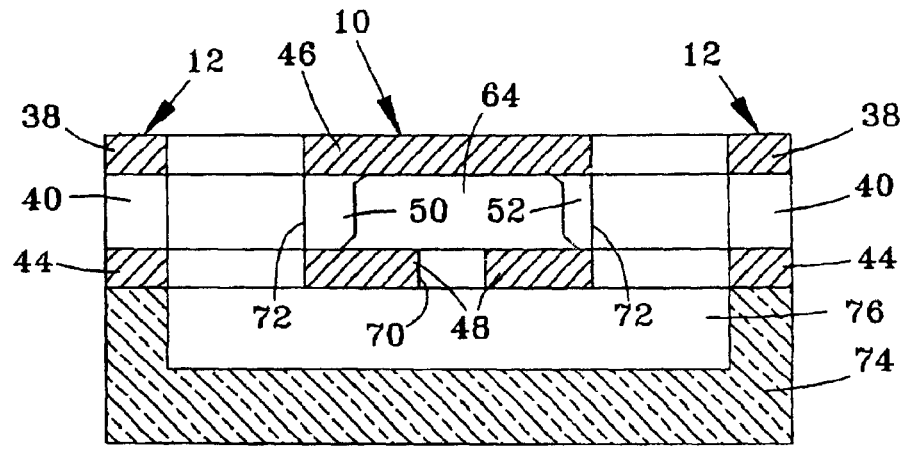

In FIG. 7, a handle wafer 74 is shown as having been bonded to the epitaxial layer 44. The wafer 74 serves to both mechanically support the structure formed by the epitaxial layers 38, 40 and 44, and to chemically protect the etched surface of this structure. For this purpose, the wafer 74 is formed to have a recess 76 that encloses the opening 70 and trench 72, such that the cavity 64, opening 70 and trench 72 are protected during subsequent etching, during which the substrate 36 is removed to expose the epitaxial layer 38 (FIG. 8). A suitable material for the wafer 74 is glass, such as the borosilicate glass commercially available under the name PYREX. A suitable technique is anodic bonding in accordance with known practices.

In FIG. 8, the substrate 36 has been removed, and that portion the epitaxial layer 38 over the cavity 64 and exposed as a result of removing the substrate 36 is identified as defining the wall 46 of the cannula 10 opposite the ports 20 and 22 in FIG. 9. FIG. 8 also shows the completion of the trench 72 that defines the outer perimeter of the cannular 10. This step entails final alignment, patterning and anisotropically etching though the surface of the epitaxial layer 38, with the etch being aligned with the existing trench 72 so that at the completion of the etch the trench 72 extends completely through the epitaxial layer 38 (wall 46) and the epitaxial layer 40. The epitaxial layer 38 is preferably masked during the etching process so that the tabs 14 remain to support the cannula 10 within the frame 12, which is defined by the remaining portions of the epitaxial layers 38, 40 and 44 surrounding the trench 72. As such, the tabs 14 are formed by the epitaxial layers 38 and 40. The tabs 14 are preferably sufficiently narrow so that minimal effort is required to singulate the cannula 10 from the frame 12.

As a result of the etch process, the wall 46 of the cannula 10 is isolated from the remainder of the epitaxial layer 38, and the sidewalls 50 and 52 are delineated from the opposing walls 62 that were defined in the epitaxial layer 40 by the cavity 64. The sidewalls 50 and 52 can be seen as being separated by the cavity 64 and sandwiched between the walls 46 and 48. A suitable thickness for each of the sidewalls 50 and 52 is roughly that of the walls 46 and 48, and therefore the epitaxial layers 38 and 44, i.e., about five to twenty micrometers. From FIG. 8, the thicknesses of the sidewalls 50 and 52 can be seen as being established by the alignment, location and width of the trench 72. For this reason, a plasma etch is again preferably used to complete the trench 72. As a result of the walls 46, 48, 50 and 52 of the cannula 10 having substantially uniform thicknesses and the cavity 60 and the trench 72 being defined by anisotropic etching, the cavity 64 defines an internal passage within the cannula 10 having a substantially rectangular cross-section and the piercing end 16 has a tapered width in a direction parallel to the walls 46 and 48 and a substantially uniform thickness in a direction normal to the walls 46 and 48.

While the invention has been described in terms of a preferred embodiment, it is apparent that other forms could be adopted by one skilled in art. For example, the physical configuration of the cannula 10 could differ from that shown, and materials and processes other than those noted could be used. Therefore, the scope of the invention is to be limited only by the following claims.

What is claimed is:

1. A device having a needle member comprising:
   a piercing end and an oppositely-disposed second end;
   an internal passage having a first opening adjacent the piercing end;
   first and second walls separated by the passage, each of the first and second walls being formed of doped single-crystal silicon-based material; and
   first and second sidewalls separated by the passage and sandwiched between the first and second walls, each of the first and second sidewalls being formed of single-crystal silicon-based material and being more lightly doped than the first and second walls.

2. A device according to claim 1, wherein the second wall is fusion bonded to the first and second sidewalls.

3. A device according to claim 1, wherein the first wall is epitaxially aligned with the first and second sidewalls.

4. A device according to claim 1, wherein the first and second walls and the first and second sidewalls are doped p-type or n-type.

5. A device according to claim 1, wherein the first opening of the passage is in the second wall of the needle member.

6. A device according to claim 1, further comprising a second opening to the passage and adjacent the second end of the passage.

7. A device according to claim 6, wherein the first and second openings of the passage are in the second wall of the needle member.

8. A device according to claim 1, further comprising at least one electrode on the second wall of the needle member, the at least one electrode having a first end adjacent the first opening of the passage and a second end adjacent the second end of the needle member.

9. A device according to claim 1, wherein the passage has a rectangular cross-section.

10. A device according to claim 1, wherein the piercing end of the needle member is defined by a tapered width in a direction parallel to the first and second walls and a substantially uniform thickness in a direction normal to the first and second walls.

11. A device according to claim 1, further comprising a frame surrounding the needle member, the frame comprising first and second layers and an inner layer separating the first and second layers, the first layer being coplanar with the first wall and formed of the same doped silicon-based single-crystal material as the first wall, the second layer being coplanar with the second wall and formed of the same doped single-crystal silicon-based material as the second wall, and the inner layer being coplanar with the first and second sidewalls and formed of the same single-crystal silicon-based materials as the first and second sidewalls.

12. A device according to claim 11, further comprising tabs interconnecting the inner layer of the frame with the first and second sidewalls of the needle member so as to suspend the needle member from the frame.

13. A device according to claim 12, further comprising a support member bonded to the second layer of the frame, the support member defining a cavity over which the needle member is suspended by the tabs.

14. A device having a needle member comprising:

an internal passage having a rectangular cross-section and first and second openings;

first and second walls separated by the passage, each of the first and second walls being formed of doped single-crystal silicon-based material;

first and second sidewalls separated by the passage and sandwiched between the first and second walls, each of the first and second sidewalls being formed of single-crystal silicon-based material and being more lightly doped than the first and second walls, the first and second sidewalls being fusion bonded to the second wall, the first wall being epitaxially aligned with the first and second sidewalls;

a piercing end adjacent the first opening of the passage, the piercing end being defined by a tapered width in a direction parallel to the first and second walls and a substantially uniform thickness in a direction normal to the first and second walls.

15. A device according to claim 14, wherein the first and second walls and the first and second sidewalls are doped to be p-type or n-type.

16. A device according to claim 14, wherein the first and second openings of the passage are in the second wall of the needle member.

17. A device according to claim 14, further comprising at least one electrode on the second wall of the needle member, the at least one electrode having a first end adjacent the first opening of the passage.

18. A device according to claim 14, further comprising a frame surrounding the needle member, the frame comprising first and second layers and an inner layer separating the first and second layers, the first layer being coplanar with the first wall and formed of the same doped single-crystal silicon-based material as the first wall, the second layer being coplanar with the second wall and formed of the same doped single-crystal silicon-based material as the second wall, and the inner layer being coplanar with the first and second sidewalls and formed of the same single-crystal silicon-based material as the first and second sidewalls.

19. A device according to claim 18, further comprising tabs formed of a silicon-based material and interconnecting the inner layer of the frame with the first and second sidewalls of the needle member so as to suspend the needle member from the frame.

20. A device according to claim 19, further comprising a support member bonded to the second layer of the frame, the support member defining a cavity over which the needle member is suspended by the tabs.

* * * * *